United States Patent [19]

Tsou

[11] Patent Number: 4,754,749
[45] Date of Patent: Jul. 5, 1988

[54] SURGICAL SCREW WITH COUNTER-ROTATION PREVENTION MEANS

[76] Inventor: Paul M. Tsou, 526 Adelaide Dr., Santa Monica, Calif. 90404

[21] Appl. No.: 856,988

[22] Filed: Apr. 29, 1986

[51] Int. Cl.⁴ .......................... A61F 5/04; F16B 39/00
[52] U.S. Cl. ........................... 128/92 YE; 128/92 YS; 411/83; 411/403
[58] Field of Search ....... 128/92 YW, 92 YU, 92 YS, 128/92 YE, 92 YF, 92 R, 92 VY, 92 Y; 433/174, 175, 176; 411/403, 83, 358, 364, 400, 132

[56] References Cited

U.S. PATENT DOCUMENTS

| | | | |
|---|---|---|---|
| 324,768 | 8/1885 | Hunt | 128/92 YF |
| 2,242,003 | 5/1941 | Lorenzo | 128/92 YV |
| 2,355,900 | 8/1944 | Beede | 411/83 |
| 3,424,212 | 1/1969 | Kemper | 411/403 |
| 3,474,537 | 10/1969 | Christensen | 433/174 |
| 3,579,831 | 5/1971 | Stevens et al. | 128/92 YS |

FOREIGN PATENT DOCUMENTS 565144 1/1924 France ................... 411/83

OTHER PUBLICATIONS

Depuy Manufacturing Company Inc., Warsaw, Ind., sales catalog, p. 126.

*Primary Examiner*—John D. Yasko
*Assistant Examiner*—Ralph Lewis
*Attorney, Agent, or Firm*—B. F. Spencer

[57] ABSTRACT

A unitary surgical screw is disclosed for the internal fixation of an acromio-clavicular separation by mechanically maintaining the clavicle in a fixed position with respect to the coracoid once the separation has been reduced. The surgical screw includes a short, cylindrical head; a smooth, cylindrical shank portion; and a helically threaded distal end portion. A transverse slot is recessed partially into the top surface of the head of the screw. One or more inclined holes extend through the head of the screw from the bottom of the transverse slot to the underside of the head. After the separation has been reduced and the screw properly installed, a locking pin is inserted through one of the inclined holes and staked to the clavicle to prohibit rotation of the screw. The surgical screw may include an axial bore, concentric with the longitudinal axis of the screw, for receiving an elongated guide pin for aiding the axial alignment of the screw prior to its installation.

3 Claims, 1 Drawing Sheet 4,754,749

SURGICAL SCREW WITH COUNTER-ROTATION PREVENTION MEANS

BACKGROUND OF THE INVENTION

The present invention relates to surgical screws, and, in particular, to means for preventing counter-rotation of a surgical screw during the period that it remains in its installed position within the patient.

Surgical screws used in the fixation of bone fractures and separations occurring in a patient are well-known in the art. One representative example of a surgical screw used in the fixation of hip fractures is disclosed in U.S. Pat. No. 2,570,465. This prior art surgical screw has a generally flat head with a smooth, frusto-conical under surface, a smooth, cylindrical shank, and a helically threaded distal end portion. The screw is installed through a pre-drilled bore extending from the femur through the center of the hip fracture in the femoral neck and into the center of the ball-shaped head seated within a socket in the pelvic bone. The screw may include an axial bore extending completely through the center of the screw for receiving a long guide pin used to axially align the screw prior to its installation. An additional surgical screw for the fixation of fractures of the femoral neck is disclosed in U.S. Pat. No. 4,383,527. ther surgical screws known in the art include the Mecron and the Howse cannulated screws.

The surgical screw of the present invention differs from the above-mentioned surgical screws in that its principal use is for the internal fixation of an acromioclavicular separation. The improved screw is installed to maintain the clavicle in a fixed position with respect to the coracoid once the separation has been reduced. To prevent counter-rotation of the screw while in place within the patient, one or more inclined holes or bores are provided through the head of the screw. A long, slender locking pin is inserted into and through an appropriate one of the inclined holes into a small pre-drilled hole within the clavicle; the axis of the hole in the head of the screw being inclined with respect to the longitudinal axis of the screw, enabling the long, slender locking pin to be staked into the clavicle to prevent counter-rotation of the screw. Any counter-rotation or loosening of the screw, once installed, seriously jeopardizes the reduction of the separation and a prompt recovery.

Accordingly, the principal object of the present invention is to provide a surgical screw which can be retained in its installed position without the risk of counter-rotation during the period that the screw must remain in place within the patient.

The above object of and the brief introduction to the present invention will be more fully understood, and further objects and advantages will become apparent, from a study of the following detailed description in connedtion with the drawings.

DESCRIPTION OF THE INVENTION

Figures 1, 2:
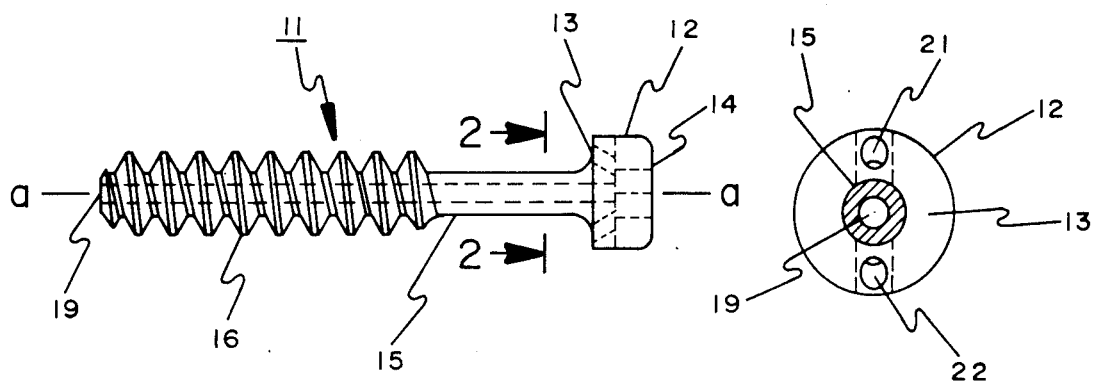
FIG. 1 is a side view of the improved surgical screw of the invention.
FIG. 2 is an enlarged view of the under surface of the head portion of the surgical screw of FIG. 1 taken along the line 2—2.

Referring to FIGS. 1-4 of the drawing, the improved unitary surgical screw 11 includes a short, cylindrical head portion 12 having a substantially flat under surface 13 and a partially rounded top surface 14. Screw 11 includes a smooth, cylindrical shank portion 15, one end of which is integrally attached to the center of flat under surface 13. The distal end portion of screw 11 includes a helically threaded portion 16. The outer diameter of helically threaded portion 16 is larger than the diameter of shank portion 15 and smaller than the diameter of head portion 12, as shown in FIG. 1.

Figures 3, 4:
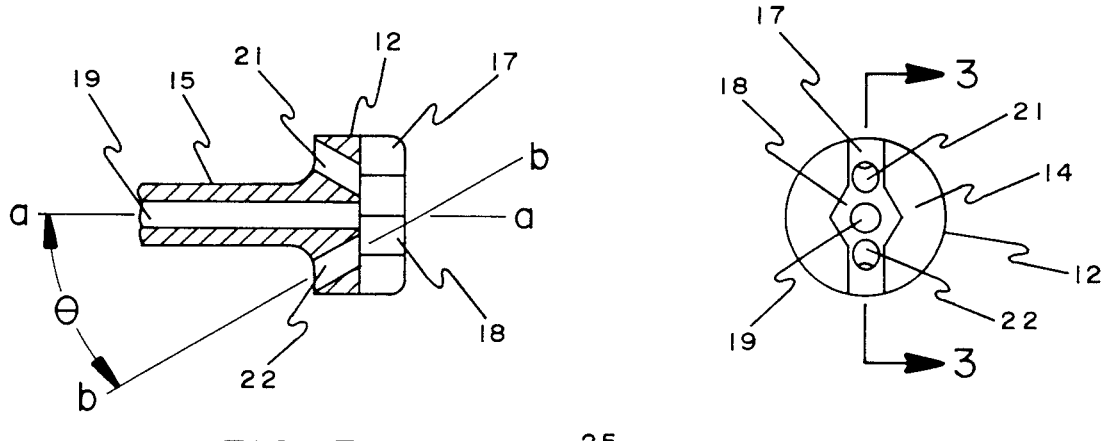
FIG. 3 is an enlarged sectional view of the shank and head portions of the surgical screw taken along the lines 3—3 of FIG. 4.
FIG. 4 is an enlarged view of the top surface of the head of the screw showing the transverse slot, the central hexagonal socket, the axial bore and the inclined holes.

A transverse slot 17 is partially recessed into head portion 12 from rounded top surface 14, as seen in FIGS. 3 and 4, for receiving a screw driver tool for rotating and installing screw 11. The center of head portion 12 is provided with a hexagonal, countersunk socket 18 extending from rounded top surface 14 to the bottom of transverse slot 17, as seen in FIGS. 3 and 4. Hexagonal, countersunk socket 18 is adapted for receiving a conventional hexagonal tool, of the Allen type.

An axial bore 19 extends completely through the center of surgical screw 11 from the bottom of transverse slot 17 in head portion 12 to the tip of helically threaded portion 16, as seen in FIG. 1. The diameter of axial bore 19 is appreciably less than the diameter of shank portion 15. Axial bore 19 is coaxial with the longitudinal axis a—a of screw 11 and is adapted for sliding over a long guide pin (not shown). The guide pin is used in the alignment of the holes to be placed through the clavicle and into the coracoid into which surgical screw 11 is to be installed.

First and second inclined holes or bores 21 and 22 extend through head portion 12 of screw 11 from the bottom of transverse slot 17 to the under surface 13. The axis b—b of each inclined hole 21 and 22 is inclined with respect to the longitudinal axis a—a of screw 11 by an angle $\theta$ of approximately thirty degrees, as seen in FIG. 3. The diameter of inclined holes 21 and 22 is slightly less than the diameter of axial bore 19. As can be seen in FIGS. 1-4, the two inclined holes 21 and 22 are displaced from and are diametrically disposed with respect to axial bore 19. Each inclined hole exits the under surface 13 near the peripheral edge of head portion 12.

Figure 5:
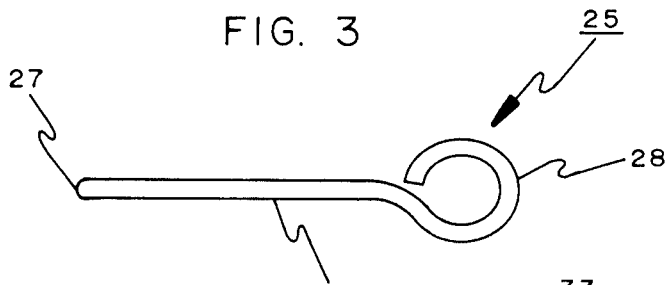
FIG. 5 is an enlarged view of the locking pin for use with the improved surgical screw.

Referring to FIG. 5, a long, slender locking pin 25, having a smooth shank 26, a rounded distal tip 27, and a closed-loop proximal end 28, is dimensioned to be inserted into one of the first or second inclined holes 21 or 22. The closed-loop proximal end 28 is intended to fit within the transverse slot 17 when the plane of closed-loop end 28 is aligned with the plane of transverse slot 17.

Figure 6:
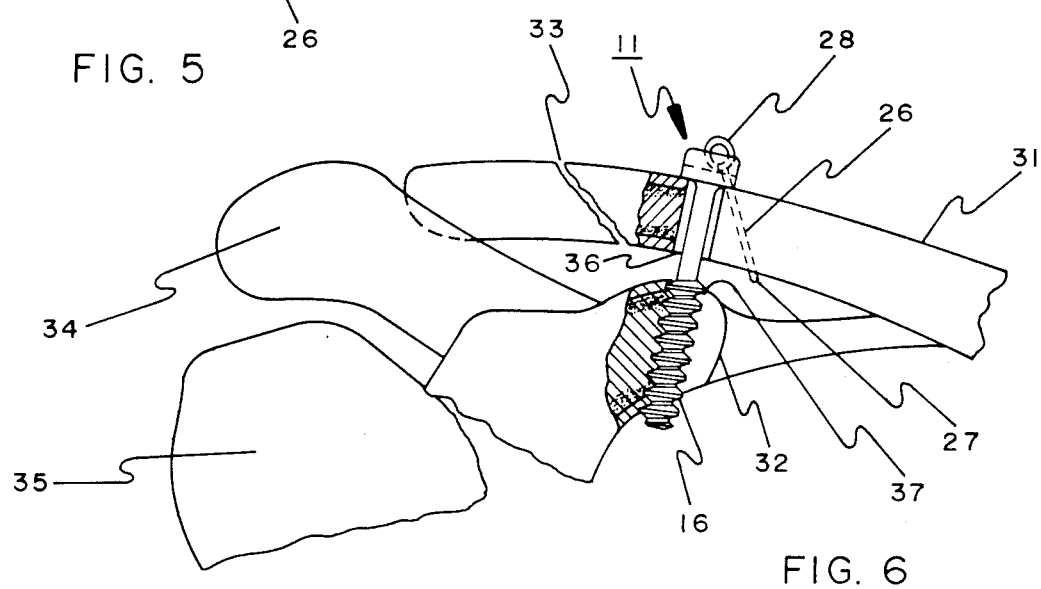
FIG. 6 is a view of the surgical screw installed to maintain the clavicle in a fixed position with respect to the coracoid and showing the locking pin in its installed position.

FIG. 6 illustrates a representative installation of surgical screw 11 and locking pin 25 within a patient to maintain clavicle 31 in a fixed position with respect to coracoid 32. The separation 33 in clavicle 31 appears at the left side of surgical screw 11, the left end of clavicle 31 being attached by ligaments to acromion 34. The humerus 35 of the patient appears directly below acromion 34.

Prior to installation of surgical screw 11, a hole 36 is carefully located and drilled in the center of clavicle 31 directly over the thickest portion of coracoid 32. The diameter of hole 36 is somewhat larger than the diameter of shank portion 15 of surgical screw 11, as shown, to provide ample clearance between hole 36 and shank portion 15. A long guide pin is employed to locate and align the correct position upon coracoid 32 into which a second hole 37 is drilled. A cannulated drill is inserted over the long guide pin to drill second hole 37. Upon completion of second hole 37, the cannulated drill is carefully removed leaving the long guide pin in place. The axial bore 19 of surgical screw 11 is then placed over the long guide pin to lead helically threaded portion 16 into the correct position for entering second hole 37. A conventional cannulated screw driver is employed to engage transverse slot 17 of screw 11. The axial bore of the cannulated screw driver is carefully aligned and placed over the long guide pin, being careful to maintain the alignment and orientation of the guide pin, to insure correct alignment of surgical screw 11 as it is rotated and advanced into position, as shown in FIG. 6.

After separation 33 has been correctly reduced by proper adjustment of screw 11, locking pin 25 can be installed to prevent counter-rotation of screw 11. A small, inclined pilot hole is drilled into and through clavicle 31 by passing the drill through one of the first or second inclined holes 21 or 22. It is preferred that the small pilot hole be drilled in the portion of clavicle 31 extending toward the head of the patient to provide clearance for the drilling operation and for installing pin 25. After the pilot hole has been drilled, the round distal tip 27 and shank 26 of pin 25 are passed through the selected hole 21 or 22 in head portion 12. By lightly tapping the closed-loop proximal end 28, as with a hammer, pin 25 can be driven into position. The plane of closed-loop end 28 is aligned with that of transverse slot 17 in order that closed-loop end 28 can recess in and rest upon the bottom of transverse slot 17, as shown in FIG. 6.

The central opening or eye of closed-loop end 28 greatly facilitates the ease by which pin 25 may be removed. A relatively simple incision through the patient's skin directly over the top of screw 11 enables the physician to insert an appropriate tool to grip closed-loop end 28 and extract pin 25. It should be noted that closed-loop end 28 of pin 25 lies within transverse slot 17 and directly over hexagonal socket 18. Removal of pin 25 must be completed before it is possible for a tool to enter either transverse slot 17 or hexagonal socket 18. The conventional hexagonal Allen wrench may be employed to remove screw 11 from the patient by insertion into hexagonal socket 18 after the acromio-clavicular separation has healed.

Surgical screw 11 and locking pin 25 are made of medically approved stainless steel. A representative example appears in the following table.

| Identification of Part | Diameter in Millimeters |
| --- | --- |
| Length of screw 11 | 30-40 |
| Diameter of head portion 12 | 9 |
| Length of head portion 12 | 5 |
| Diameter of shank portion 15 | 3.5 |
| Length of shank portion 15 | 10-13.5 |
| Diameter of threaded portion 16 | 5.5-7.0 |
| Length of threaded portion 16 | 20-25 |
| Width of transverse slot 17 | 2 |
| Depth of transverse slot 17 | 2.5 |
| Diameter of axial bore 19 | approx. 2 |
| Pitch of threads of portion 16 | approx. 2.4 |
| Diameter of inclined holes 21,22 | approx. 1.8 |
| Length of locking pin 25 | 25-30 |
| Diameter of shank 26 of pin 25 | approx. 1.6 |

It will be appreciated that the length of screw 11, including its shank and threaded portion 15,16, as well as the diameter of threaded portion 16, will be dependent upon the age and physical size of the patient.

While the improved surgical screw 11 and its locking pin 25 have been illustrated for use in maintaining the clavicle in a fixed position with respect to the coracoid for the internal fixation of an acromio-clavicular separation, it is apparent that the present invention is not restricted to this illustrated example and may find additional uses. For example, the improved surgical screw may be used for the internal reduction of a fracture in the distal end of the clavicle.

Since many changes may be made in the above-described apparatus and many different embodiments of this invention could be made without departing from the scope thereof, it is intended that all matter contained in the above description or shown in the accompanying drawings shall be interpreted as illustrative and not in a limiting sense.

What is claimed is:

1. The combination for the internal fixation of an acromio-clavicular separation in a patient by physically maintaining the clavicle in a fixed position with respect to the coracoid after the fracture has been reduced, comprising:
    (a) a unitary surgical screw having a short, cylindrical head protion, a smooth, cylindrical shank portion, and a helically threaded distal end portion; the short, cylindrical head protion having a substantially flat under surface and a partially rounded top surface;
    (b) a hexagonal, countersunk socket extending part way into the center of the short, cylindrical head portion from the rounded top surface;
    (c) a transverse slot recessed partially into the short, cylindrical head portion from the rounded top surface;
    (d) an inclined hole extending through the short, cylindrical head protion, said inclined hole extending from the bottom of said transverse slot to the flat under surface of the short, cylindrical head portion, the axis of said inclined hole being inclined with respect to the longitudinal axis of said screw by an acute angle; and
    an elongated pin means having a smooth, cylindrical shank portion of uniform diameter, a rounded distal tip portion and a curved loop proximal end portion, the smooth cylindrical shank portion being adapted for insertion into and through said inclined hole without bending, after said surgical screw has been properly installed, for staking the rounded distal tip portion into the clavicle to prevent rotation of said surgical screw relative to the clavicle; the curved loop proximal end portion of said elongated pin means being retained in said transverse slot and over said hexagonal countersunk socket to restrict rotational movement of said elongated pin means about its longitudinal axis and to prohibit entry of a removal tool into said transverse slot and said hexagonal countersunk socket as long as said elongated pin means remains in its installed position, a portion of the curved loop end of said elongated pin means protruding above the rounded top surface of the head of said screw to enable a removal tool to physically engage the curved loop end in order to extract said elongated pin means, thereby allowing said surgical screw to be removed from the patient after the acromio-clavicular separation has been healed.

2. The combination for the internal fixation of an acromio-clavicular separation as defined by claim 1 wherein said unitary surgical screw further includes an axial bore extending completely through the center of said screw from said cylindrical head portion to said helically threaded portion, said axial bore being concentric with the smooth, cylindrical shank portion and being adapted for receiving a long guide pin for aiding the axial alignment of said screw prior to its installation.

3. The combination for the internal fixation of an acromio-clavicular separation as defined by claim 1 further comprising an additional inclined hole extending through the short, cylindrical head portion, said additional inclined hole being diametrically disposed with respect to said inclined hole about said hexagonal countersunk socket, said additional inclined hole extending from the bottom of said transverse slot to the flat under surface of the short, cylindrical head portion, the axis of said additional hole being inclined with respect to the longitudinal axis of said screw by an acute angle; and wherein the rounded distal tip portion of said elongated pin means is adapted for insertion into and through one of said inclined holes after said surgical screw has been properly installed for staking the rounded distal tip portion into the clavicle.

* * * * *